(12) United States Patent
Sidebottom et al.

(10) Patent No.: US 6,774,210 B1
(45) Date of Patent: Aug. 10, 2004

(54) FROZEN FOOD PRODUCT

(75) Inventors: Christopher M Sidebottom, Bedford (GB); Margaret F Smallwood, York (GB); Louise J. Byass, Edmonton (CA)

(73) Assignee: Good Humor-Breyers Ice Cream Division of Conopco., Inc., Greenbay, WI (US)

( * ) Notice: Subject to any disclaimer, the term of this patent is extended or adjusted under 35 U.S.C. 154(b) by 0 days.

(21) Appl. No.: 09/582,296

(22) PCT Filed: Dec. 23, 1998

(86) PCT No.: PCT/EP98/08554

§ 371 (c)(1),
(2), (4) Date: Dec. 5, 2000

(87) PCT Pub. No.: WO99/37673

PCT Pub. Date: Jul. 29, 1999

(30) Foreign Application Priority Data

Jan. 22, 1998 (GB) .............................. 9801420

(51) Int. Cl.$^7$ ............................. C07K 14/41; A23G 9/02
(52) U.S. Cl. ....................... 530/326; 530/300; 530/327; 530/328; 426/565; 426/139; 426/104; 426/101; 426/100; 514/1; 514/2
(58) Field of Search ................................ 530/350, 300, 530/326, 327, 328; 426/100, 101, 104, 139, 565; 514/1, 2

(56) References Cited

U.S. PATENT DOCUMENTS 5,169,783 A    12/1992    Kieft
5,676,985 A  * 10/1997    Fletcher ........................ 426/36
6,096,867 A  *  8/2000    Byass .......................... 530/350

FOREIGN PATENT DOCUMENTS

| WO | WO 92/22581 |   | 12/1992 |
| WO | WO 94/14472 | * | 7/1994  |
| WO | WO 96/39878 | * | 12/1996 |
| WO | WO 98/04148 |   | 2/1998  |

OTHER PUBLICATIONS

Alkhatib, Virology, 1986, 150, pp. 479–490.*
Lazar, et al. Transforming growth factor alpha:mutation of aspartic acid 47 and leucine 48 result in different biological activities Molecular and Cellular Biology, 1998, vol. 8, No. 3, pp. 1247–1252.
Griffith M et al: "Antifreeze proteins and their potential use in frozen foods" Biotechnology Advances, vol. 13, No. 3, Jan. 1, 1995 XPP004045399 ISSN: 0734-9750 abstract.
Feeney R E et al: "Antifreeze Proteins: Properties, Mechanism of Action, and Possible Applications" Food Technology, vol. 47, No. 1, Jan. 1, 1993, pp. 82, 84–88, 90, XP002040501 ISSN: 0015–6639.

* cited by examiner

*Primary Examiner*—Christopher Tate
*Assistant Examiner*—Roy Teller
(74) *Attorney, Agent, or Firm*—Morgan Lewis & Bockius LLP

(57) ABSTRACT

Anti-freeze protein which can be derived from Lichen, said protein having an apparent molecular weight of from 20 to 28 kDa and having an N-terminal amino acid sequence which shows at least 80% overlap with: A-P-A-V-V-M-G-D-A-E-S-F-G-A-I-A-H-G-G-L and modified versions and isoforms of this protein.

19 Claims, No Drawings

SEQUENCE LISTING

<160> NUMBER OF SEQ ID NOS: 2

<210> SEQ ID NO 1
<211> LENGTH: 18
<212> TYPE: PRT
<213> ORGANISM: Umbilicaria antarctica

<400> SEQUENCE: 1

Ala Pro Ala Trp Met Asp Ala Glu Ser Phe Gly Ala Ile Ala His Gly
1               5                   10                  15

Gly Leu

<210> SEQ ID NO 2
<211> LENGTH: 20
<212> TYPE: PRT
<213> ORGANISM: Umbilicaria antarctica

<400> SEQUENCE: 2

Ala Pro Ala Val Val Met Gly Asp Ala Glu Ser Phe Gly Ala Ile Ala
1               5                   10                  15

His Gly Gly Leu
            20

FROZEN FOOD PRODUCT

This application is the national phase of international application PCT/EP98/08554 filed Dec. 23, 1998 which designated the U.S.

TECHNICAL FIELD OF THE INVENTION

The invention relates to anti-freeze proteins (AFPs) and frozen food product containing AFPs.

BACKGROUND TO THE INVENTION

Anti-freeze proteins (AFPs) have been suggested for improving the freezing tolerance of foodstuffs.

For the purpose of the invention, the term AFP has the meaning as well-known in the art, namely those proteins which exhibit the activity of inhibit the growth of ice crystals. See for example U.S. Pat. No. 5,118,792.

WO 90/13571 discloses antifreeze peptides produced chemically or by recombinant DNA techniques. The AFPs can suitably be used in food-products.

WO 92/22581 discloses AFPs from plants which can be used for controlling ice crystal shape in ice-cream. This document also describes a process for extracting a polypeptide composition from extracellular spaces of plants by infiltrating leaves with an extraction medium without rupturing the plants.

WO 94/03617 discloses the production of AFPs from yeast and their possible use in ice-cream. WO 96/11586 describes fish AFPs produced by microbes.

Several literature places also mention the isolation and/or use of plant proteins for cryoprotection. Cryoprotective proteins have a function in the protection of plant membranes against frost damage. These proteins, however, do not possess recrystallisation inhibition properties and are, therefore, not embraced within the terms AFPs.

Hincha in Journal of Plant Physiology, 1992, 140, 236–240 describes the isolation of cryoprotective proteins from cabbage. Volger in Biochimica et Biophysica Acta, 412 (1975), 335–349 describes the isolation of cryoprotective leaf proteins from spinach. Boothe in Plant Physiol (1995), 108: 759–803 describes the isolation of proteins from *Brassica napus*. Again, these proteins are believed to be cryoprotective proteins rather than AFPs. Neven in Plant Molecular Biology 21: 291–305, 1993 describes the DNA characterisation of a spinach cryoprotective protein. Salzman in Abstracts and Reviews of the 18th Annual Meeting of the ASEV/Eastern Section in Am. J. Enol. Vitic., Vol. 44, No. 4, 1993 describes the presence of boiling-stable polypeptides in buds of Vitis. Although the proteins are analogous to fish antifreeze peptides, they are cryoprotective proteins and not AFPs. Lin in Biochemical and Biophysical Research Communication, Vol. 183, No. 3, 1992, pages 1103–1108 and in Lin, Plant Physiology (1992) 99, 519–525 describes the 15 kDa cryoprotective polypeptide from Arabidopsis Hakaira. Houde in The Plant Journal (1995) 8(4), 583–593 mentions cryoprotective proteins from wheat.

Up till now, however the use of AFPs has not been applied to commercially available food products. One reason for this are the high costs and complicated process for obtaining AFPs. Another reason is that the AFPs which until now have been suggested for use in frozen food products cannot be incorporated in the standard formulation mix, because they tend to destabilise during processing especially during the pasteurisation step. This destabilisation is believed to be caused by the denaturation of the AFPs; this is a well-known effect commonly observed for peptides and proteins.

In our non pre-published patent application: WO 98/4148 it has been described that particularly good AFPs can be isolated from natural sources such as Lichen.

Applicants have now been able to determine the partial amino acid sequence of a particularly active AFP from Lichen.

Accordingly the invention relates to an AFP which can be derived from Lichen, said AFP having an apparent molecular weight of about 24 kDa and an amino acid sequence from the N-terminus of: A-P-A-W-M-D-A-E-S-F-G-A-I-A-H-G-G-L (SEQ ID NO:1).

Also embraced in the scope of our invention are proteins having a sequence which has a high degree of similarity with the above sequence. For the purpose of the invention all RI active proteins having an amino acid sequence of at least 80% overlap with the above sequence are also embraced in the scope of the invention. More preferred is an overlap of at least 90%, most preferred more than 95%, e.g. those amino acid sequences which differ none or only one or two amino acids with the above sequence.

For the purpose of the invention the degree of overlap of two (partial) amino acid sequences can be calculated as follows:

(a) the two amino acid sequences are aligned and the number of amino acids which are identical and appear in the same order are counted (X)

(b) every change, deletion or addition of an amino acid is counted as 1 point, and the total of changes, deletions and additions is calculated (Y)

(c) the degree of overlap can now been calculated as X*100%/(X+Y).

For example the (partial) amino acid sequence from the N-terminus of: A-P-A-V-V-M-G-D-A-E-S-F-G-A-I-A-H-G-G-L (SEQ ID NO:2), can be aligned with the control as follows:

A-P-A-V-V-M-G-D-A-E-S-F-G-A-I-A-H-G-G-L (SEQ ID NO:2)

A-P-A-W -M- D-A-E-S-F-G-A-I-A-H-G-G-L (SEQ ID NO:1).

This leads to a total number of identical amino acids in the same order of 17. The number of changes is 1 (W into V at the fourth position); the number of additions is 2 (V at fifth position, G at 7th position), while there are no deletions. The total of changes, additions and deletions is therefore 3. This leads to a degree of overlap of 17*100%/(17+3)=85%

The protein having (partial) amino acid sequence from the N-terminus of:

A-P-A-V-V-M-G-D-A-E-S-F-G-A-I-A-H-G-G-L (SEQ ID NO:2) is hence also embraced within the invention.

Also embraced within the scope of the present invention are modified versions of the above described proteins whereby said modification does not materially affect the ice recrystallisation inhibition properties, such as glycosylated versions thereof.

For the purpose of the invention the term about 24 kDa molecular weight means any molecular weight from 20 to 28 kDa as measured on SDS-PAGE using standard reference markers, more preferably the molecular weight is from 22 to 26 kDa.

The advantageous AFP of the present invention can be derived from Lichen especially from the species *Umbilicaria antarctica*.

Also embraced within the scope of the present invention are anti-freeze proteins which although originally derived from Lichen are produced by other methods, for example by genetic modification techniques whereby for example microorganisms or plants are genetically modified to produce the above described proteins. These proteins are also embraced within the term "can be derived from Lichen".

Also embraced within the scope of the present are nucleic acid sequences which are capable to encode the above described AFPs.

Vectors containing a nucleic acid sequence capable of encoding the AFP of the invention are also embraced within the scope of the invention.

Based on the above information it is also possible to genetically modify other natural sources such that they produce the advantageous AFP as identified here-above.

Applicants also have found that AFPs of the above sequence have improved ice-recrystallisation inhibition properties. A suitable test for determining the ice recrystallisation inhibition properties is described in the examples and involves the quick freezing to at least $-40°$ C., for example $-80°$ C. followed by storage for one hour at $-60°$ C. Preferably AFPs in accordance to the invention provide a ice particle size following an ice recrystallisation inhibition assay—as described in the examples—of 15 VM or less, more preferred from 5 to 15 $\mu$m.

The AFP of the invention can conveniently be used in food products, preferably in food products which are frozen or intended to be frozen. Especially preferred is the use of AFPs in products which are heated e.g. by pasteurisation or sterilisation prior to freezing. Especially preferred is the use in frozen confectionery products.

Examples of such food products are: frozen confectionery mixes such as ice-cream mixes and water-ice mixes which are intended to be pasteurised prior to freezing. Such mixes are usually stored at ambient temperature. Suitable product forms are for example: a powder mix which is packed for example in a bag or in sachets. Said mix being capable of forming the basis of the frozen food product e.g. after addition of water and optionally other ingredients and—optional—aeration.

Another example of a suitable mix could be a liquid mix (optionally aerated) which, if necessary after addition of further components and optional further aeration can be frozen.

The clear advantage of the above mentioned mixes is that the presence of the AFP ingredient makes that the mixes can be frozen under quiescent conditions, for example in a shop or home freezer without the formation of unacceptable ice crystal shapes and hence with a texture different to products normally obtained via quiescent freezing.

Very conveniently these mixes are packed in closed containers (e.g. cartons, bags, boxes, plastic containers etc.). For single portions the pack size will generally be from 10 to 1000 g. For multiple portions pack sizes of up to 500 kg may be suitable. Generally the pack size will be from 10 g to 5000 g.

As indicated above the preferred products wherein the AFPs are used are frozen confectionery product such as ice-cream or water-ice. Preferably the level of AFPs is from 0.00001 to 0.5 wt % based on the final product. If dry-mixes or concentrates are used, the concentration may be higher in order to ensure that the level in the final frozen product is within the above ranges.

For the purpose of the invention the term frozen confectionery product includes milk containing frozen confections such as ice-cream, frozen yoghurt, sherbet, sorbet, ice milk and frozen custard, water-ices, granitas and frozen fruit purees. For some applications the use in fermented food products is less preferred.

Preferably a the level of solids in the frozen confection (e.g. sugar, fat, flavouring etc.) is more than 4 wt %, for example more than 30 wt %, more preferred from 40 to 70 wt %.

Frozen confectionery products according to the invention can be produced by any method suitable for the production of frozen confectionery. Especially preferably however all the ingredients of the formulation are fully mixed before pasteurisation and before the freezing process starts. The freezing process may advantageously involve a hardening step, for example to a temperature of $-30$ Fahrenheit or lower.

EXAMPLE I

The ice recrystallisation inhibition properties of the AFPs can determined as follows:

A sample of an AFP containing product was adjusted to a sucrose level of 30 wt % (If the starting level of the sample was more than 30% this was done by dilution, if the starting level was lower sucrose was added to the 30% level).

A 3 $\mu$L drop of the sample was placed on a 22 mm coverslip. A 16 mm diameter cover-slip was then placed on top and a 200 g weight was placed on the sample to ensure a uniform slide thickness. The edges of the coverslip were sealed with clear nail varnish.

The slide was placed on a Linkham THM 600 temperature controlled microscope stage. The stage was cooled rapidly ($50°$ C. per minute) to $-40°$ C. to produce a large population of small crystals. The stage temperature was then raised rapidly ($50°$ C. per minute) to $-6°$ C. and held at this temperature.

The ice-phase was observed at $-6°$ C. using a Leica Aristoplan microscope. Polarised light conditions in conjunction with a lambda plate were used to enhance the contrast of the ice crystals. The state of the ice phase (size of ice crystals) was recorded by 35 mm photomicrography at T=0 and T=1 hour. The ice-crystal size (length) was determined by drawing around the perimeter of the crystals. The maximum length for each individual ice crystal of a batch of ice cream was imported into a spreadsheet where analysis of the data set was carried out to find the mean, and standard deviation.

Another method to test ice recrystallisation inhibition properties is as follows:

Anti-freeze activity was measured using a modified "splat assay" (Knight et al, 1988). 2.5 $\mu$l of the solution under investigation in 30% (w/w) sucrose was transferred onto a clean, appropriately labelled, 16 mm circular coverslip. A second coverslip was placed on top of the drop of solution and the sandwich pressed together between finger and thumb. The sandwich was dropped into a bath of hexane held at $-80°$ C. in a box of dry ice. When all sandwiches had been prepared, sandwiches were transferred from the $-80°$ C. hexane bath to the viewing chamber containing hexane held at $-6°$ C. using forceps pre-cooled in the dry ice. Upon transfer to $-6°$ C., sandwiches could be seen to change from a transparent to an opaque appearance. Images were recorded by video camera and grabbed into an image analysis system (LUCIA, Nikon) using a 20× objective. Images of each splat were recorded at time=0 and again after 30–60 minutes. The size of the ice-crystals in both assays was compared. If the size at 30–60 minutes is similar or only moderately increased (say less than 20% increased, more preferred less than 10% increased, most preferred less than 5% increased) compared to the size at t=0, this is an indication of good ice-crystal recrystallisation inhibition properties.

Generally these tests can be applied to any suitable composition comprising AFP and water. Generally the level of AFP in such a test composition is not very critical and can for example be from 0.0001 to 0.5 wt %, more preferred 0.0005 to 0.1 wt %, most preferred 0.001 to 0.05 wt %, for example 0.01 wt %.

Any suitable composition comprising AFP and water can be used to carry out the test. Generally, however, it will not be necessary to obtain the AFP in purified form. For practical applications normally it would suffice to prepare a liquid extract or juice of natural material, wherein this extract or juice can then be tested.

EXAMPLE II 9.5 g Umbilicaria antarctica collected during Spring 1996 from the Antarctic and stored at −20° C. was homogenised in liquid nitrogen in a mortar and pestle to a fine powder. This powder was transferred to a fresh mortar and pestle held at room temperature. Following the addition of 10 ml 0.2 M Tris HCl containing 10 mM EDTA the powder was further ground in the mortar and pestle and the homogenate filtered through 2 layers of muslin. The retentate was replaced in the mortar and pestle and a further 10 ml buffer added and the retentate ground further. This material was filtered as above and the filtrate pooled with filtrate from the first homogenisation step. The filtrate was centrifuged at 30,000 g for 15 minutes and the supernatant collected and frozen in aliquots.

0.15 g NH4SO4 was dissolved in 1 ml supernatant and the solution incubated for 30 minutes at 4 C. After centrifugation at 30,000 g for 10 minutes 0.3 g NH4SO4 was dissolved in the supernatant from this step and the solution incubated at 4 C. for 30 minutes. The solution was centrifuged at 30,000 g for 10 minutes and the supernatant discarded. The pellet was resuspended in 0.2 ml water and serial dilutions of this solution and the original extract prepared in 30% (w/w) sucrose in water for semi-quantitative splat analysis. Splat activity could be detected (by the above method) in the original extract to a dilution of more than 200 fold and in the resuspended pellet to a dilution of 800 fold indicating that more than half of the total splat activity present in the original extract had been harvested in the NH4SO4 pellet.

200 microliter 0.1 M TrisHCl pH 7.5 was added to the resuspended pellet and the solution concentrated in a 10 kDa cut-off microcon (Amicon) to 150 microliter. 100 microliter of this solution was applied to a Q-Sepharose column pre-equilibrated in 50 mM Tris HCl pH 7.5 using a SMART chromatography system (Pharmacia) at a flow rate of 100 microliter per minute and 100 microliter fractions collected. Following 800 microliter was in 50 mM Tris Hcl pH 7.5, a 0–0.5 M NaCl gradient was applied to the column over 1.5 ml and the eluate monitored at 280 nm. Following 50 fold dilution in 30 w/w % sucrose, fractions were tested for splat activity as in example I. Activity was found to correlate with a peak of OD 280 which eluted at approximately 0.1 M NaCl which was mainly collected in fraction 14.

40 microliter fraction 14 was applied to a Superdex 75 gel permeation column pre-equilibrated in 50 mM Tris HCl pH 7.5 at a flow rate of 40 microliter per minute using a SMART chromatography system (Pharmacia). The eluate was monitored at OD 280 and OD 215 and the 80 microliter fractions were collected from 0.6 ml after sample application, 50 microliter fractions between 1.1 and 1.6 ml and 100 microliter fractions between 1.6 and 3 ml. 1 microliter from each fraction was diluted 25 times in 30 w/w % sucrose and assayed for splat activity. Activity was found to correlate with a peak of OD280 and OD215 which eluted with a retention of 1.2 ml in fractions 9 and 10. The Superdex column was calibrated by determination of the retention volume (Ve) of standard protein molecular weight markers (Sigma) and the void volume (Vo) determined as 0.91 ml by application of blue dextran. A standard curve of log10 Mr against Ve/Vo was plotted and the apparent molecular weight of the OD 280 peak correlating with the lichen splat activity determined as 30 kDa.

32 microliter from fractions 9 and 10 eluting from the Superdex column were pooled and concentrated to 10 microliter in a 10 kDa cut-off microcom (Amicon) and 3.5 microliter 4× SDS-PAGE sample buffer was added to 10 microliter fractions 9 and 10 eluting from the Superdex column and to fractions 12–16 eluting from the Q-sepharose column. Following heating 95° C. for five minutes and centrifugation at 10,000 g for 3 minutes 10 microliters of each sample was loaded into wells in a 4% stacking gel and polypeptides separated by electrophoresis through a 12% 0.75 mm thick SDS-PAGE mini-gel (Biorad). Following electrophoresis the gel was stained and fixed in Coomassie Brilliant Blue and destained in methanol:acetic acid:water (1:4:5) w/w. This revealed a polypeptide of apparent Mr 24 kDa in the concentrated pooled fractions 9 and 10 eluting from the Superdex column. When the gel was silver stained using the Biorad silver stain kit according to the manufacturers instructions, a polypeptide with the same apparent Mr was detectable in fraction 14 eluting from the Q-Sepharose column and in fractions 9 and 10 eluting from the Superdex column.

Following purification of further protein using essentially the same methodology as described above, the following N-terminal amino acid sequence was obtained from the 24 kDa polypeptide:

A-P-A-V-V-M-G-D-A-E-S-F-G-A-I-A-H-G-G-L (SEQ ID NO:2).

EXAMPLE III

Crude lichen filtrate in accordance to example II was ammonium sulphate precipitated and resuspended in 0.2M Tris/HCl pH 7.5 as described above and then diluted 1/10 into one of the following buffers: 0.2M sodium citrate pH 3.0, 0.2M sodium acetate pH 4.0, 0.2M Piperazine pH 5.0, 0.2 M bisTris pH 6.0, 0.2 M triethanolamine pH 7.0, 0.2 M Tris pH 8.0, 0.2 M CHES pH 9.0, 0.2 M CAPS pH 10.0. These samples were then serially diluted ½ in the relevant buffer and the dilutions mixed 1:1 with 60% sucrose prior to splat analysis according to the second test as described in example I. Between pH 10 and pH 6.0 recrystallisation inhibition activity could be detected clearly down to a dilution of 1/320. Between pH 3.0–5.0 activity could be clearly detected to a dilution of 1/80 indicating that although the protein retains some activity at low pH, its activity is reduced by a factor of 4 at pH at or below 5.0.

EXAMPLE IV

Purified lichen antifreeze in accordance to example II protein was separated by 2 dimensional electrophoresis. Gel containing 9.2M urea, 4% acrylamide (2.66 ml 30% acrylamide 0.8% bisacrylamide), 2% deionised Triton X 100, 1% 4–7 Bio-lyte ampholyte (Biorad), 1% 3.5–10 Bio-lyte ampholyte (Biorad), 0.1% TEMED, 0.01% ammonium persulphate was polymerised in small glass tubes (Biorad). The tubes were rinsed in distilled water and inserted into a mini-gel system capable of accommodating them and the upper chamber filled with 20 mM NaOH and the lower chamber with 10mMH$_3$PO$_4$. Purified lichen sample was mixed 1:1 with first dimension sample buffer (9.2 M urea, 2.0% Triton X-100, 5% beta-mercaptoethanol, 1% 4–7 Bio-lyte ampholyte, 0.25% 3–10 Bio-lyte ampholyte) and warmed to 37° C. prior to application to one of the tube gels. To a second rod, 2 dimensional marker proteins (Biorad) were applied and to a third rod a mixture of 2 dimensional marker proteins and the lichen sample was applied. Following electrophoresis at 500V for 10 minutes lei and 750 V for 4 hours the rods were extruded from the tubes and loaded onto 3 separate 1 mm thick 12% SDS-PAGE mini gels (Biorad) and overlayed with SDS-PAGE sample buffer. Following electrophoresis the gels were silver stained using the Biorad kit according to the manufacturer's instructions. The separation revealed 3 spots on the gel in the lichen sample all with an apparent Mr of approximately 24 kDa and PI lower than 4.5.

1 dimensional isoelectric focussing of purified lichen antifreeze protein using a slab gel composed of the same components as in the first dimension gel in the 2 dimensional separation except Biolyte 3–5 ampholytes were used in the place of Biolyte 4–7 ampholytes revealed a band with an isoelectric point lower than 3.6 following silver staining.

5. The isolated protein of claim 1 wherein the protein is glycosylated.

6. The isolated protein of claim 1 wherein 0.01 percent of the protein present in a 30 percent sucrose solution cooled to minus 80° C. and then heated to minus 6° C. yields an increase in ice crystal size of less than 20 percent when the solution is kept at minus 6° C. for 30 minutes.

7. An isolated protein produced by the method of:
(a) preparing a solution extract of *Umbilicaria antarctica*,
(b) isolating a fraction of the solution extract that displays substantial ice recrystallization inhibitory activity,
(c) isolating a sample of proteins with a molecular weight of about 24 kDa and an isoelectric point of less than 4.5 from said fraction of solution extract, and
(d) isolating a protein with an N-terminal amino acid sequence which contains up to two conservative amino acid substitutions in SEQ ID NO: 1 or 2 from said sample of proteins.

8. The isolated protein of claim 7 wherein the N-terminal amino acid sequence contains one conservative amino acid substitution in SEQ ID NO: 1 or 2.

9. The isolated protein of claim 7 wherein the N-terminal amino acid sequence comprises SEQ ID NO: 1.

What is claimed is:

1. An isolated protein with a molecular weight of about 24 kDa and an isoelectric point of about less than 4.5, comprising an N-terminal amino acid sequence which contains up to two conservative amino acid substitutions in SEQ ID NO: 1 or 2, wherein the protein displays substantial ice recrystallization inhibitory activity.

2. The isolated protein of claim 1 wherein the N-terminal amino acid sequence contains one conservative amino acid substitution in SEQ ID NO: 1 or 2.

3. The isolated protein of claim 1 wherein the N-terminal amino acid sequence comprises SEQ ID NO: 1.

4. The isolated protein of claim 1 wherein the N-terminal amino acid sequence comprises SEQ ID NO: 2.

10. The isolated protein of claim 7 wherein the N-terminal amino acid sequence comprises SEQ ID NO: 2.

11. The isolated protein of claim 7 wherein the protein is glycosylated.

12. The isolated protein of claim 7 wherein 0.01 percent of the protein present in a 30 percent sucrose solution cooled to minus 80° C. and then heated to minus 6° C. yields an increase in ice crystal size of less than 20 percent when the solution is kept at minus 6° C. for 30 minutes.

13. The isolated protein of claim 7 wherein the fraction of the solution extract that displays substantial ice recrystallization inhibitory activity is isolated by column chromatography.

14. The isolated protein of claim 7 wherein the sample of proteins with a molecular weight of about 24 kDa is isolated by gel electrophoresis.

15. The isolated protein of claim 7 wherein the sample of proteins with an isoelectric point of about less than about 4.5 is isolated by isoelectric focusing.

16. An isolated protein with a molecular weight of about 12 kDa and an isoelectric point of about less than 4.5, comprising an N-terminal amino acid sequence comprising SEQ ID NO: 1, wherein the protein displays substantial ice recrystallization inhibitory activity.

17. An isolated protein with a molecular weight of about 12 kDa and an isoelectric point of about less than 4.5, comprising an N-terminal amino acid sequence comprising SEQ ID NO: 2, wherein the protein displays substantial ice recrystallization inhibitory activity.

18. A composition comprising the isolated protein of any one of claims 1, 7, 16, or 17.

19. The composition of claim 18 wherein the amount of isolated protein in the sample is about 0.00001 to about 0.5 percent weight.

* * * * *

UNITED STATES PATENT AND TRADEMARK OFFICE
CERTIFICATE OF CORRECTION

PATENT NO. : 6,774,210 B1  
DATED : August 10, 2004  
INVENTOR(S) : Christopher M. Sidebottom et al.

It is certified that error appears in the above-identified patent and that said Letters Patent is hereby corrected as shown below:

Title page,
Item [75], Inventors, "Christopher M Sidebottom" should read as -- Christopher M. Sidebottom --; and Margaret F Smallwood" should read -- Margaret F. Smallwood --;

Column 9,
Line 2, delete "12 kDa" and insert -- 24 kDa --;

Column 10,
Line 2, delete "12 kDa" and insert -- 24 kDa --.

Signed and Sealed this

Twenty-third Day of November, 2004

JON W. DUDAS
*Director of the United States Patent and Trademark Office*